(12) United States Patent
Kim et al.

(10) Patent No.: US 12,128,123 B2
(45) Date of Patent: Oct. 29, 2024

(54) MOLDABLE COMPOSITION FOR SOLID WASHING AGENT AND METHOD FOR MOLDING THE SAME

(71) Applicant: AMOREPACIFIC CORPORATION, Seoul (KR)

(72) Inventors: Daeun Kim, Yongin-si (KR); Bohyun Seo, Yongin-si (KR); Chang Jo Jung, Yongin-si (KR); Taewon Seo, Yongin-si (KR); Jiyeon Han, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 119 days.

(21) Appl. No.: 17/685,487

(22) Filed: Mar. 3, 2022

(65) Prior Publication Data
US 2022/0280409 A1 Sep. 8, 2022

(30) Foreign Application Priority Data

Mar. 5, 2021 (KR) .................. 10-2021-0029532
Feb. 4, 2022 (KR) .................. 10-2022-0014777

(51) Int. Cl.
| | | |
|---|---|---|
| A61K 8/73 | (2006.01) | |
| A61K 8/02 | (2006.01) | |
| A61K 8/19 | (2006.01) | |
| A61K 8/34 | (2006.01) | |
| A61K 8/365 | (2006.01) | |
| A61K 8/42 | (2006.01) | |
| A61K 8/46 | (2006.01) | |
| A61K 8/60 | (2006.01) | |
| A61K 8/92 | (2006.01) | |
| A61Q 19/10 | (2006.01) | |

(52) U.S. Cl.
CPC ............ *A61K 8/732* (2013.01); *A61K 8/0225* (2013.01); *A61K 8/19* (2013.01); *A61K 8/345* (2013.01); *A61K 8/365* (2013.01); *A61K 8/42* (2013.01); *A61K 8/466* (2013.01); *A61K 8/602* (2013.01); *A61K 8/731* (2013.01); *A61K 8/922* (2013.01); *A61Q 19/10* (2013.01)

(58) Field of Classification Search
CPC ........ A61K 8/732; A61K 8/0225; A61K 8/19; A61K 8/345; A61K 8/365; A61K 8/42; A61K 8/466; A61K 8/602; A61K 8/731; A61K 8/922; A61Q 19/10; C11D 1/008; C11D 1/52; C11D 1/523; C11D 1/66; C11D 1/662; C11D 1/667; C11D 1/72; C11D 1/74; C11D 1/75; C11D 3/2041; C11D 3/2065; C11D 3/225; C11D 3/228; C11D 3/222; C11D 1/76; C11D 1/825; C11D 3/042; C11D 3/2044; C11D 3/2048; C11D 3/2068; C11D 3/2079; C11D 3/2082; C11D 3/2086; C11D 3/2093; C11D 3/3707; C11D 3/3761; C11D 3/38; C11D 3/382; C11D 11/00; C11D 11/0082; C11D 17/00; C11D 17/02; C11D 17/06
See application file for complete search history.

(56) References Cited

U.S. PATENT DOCUMENTS

| | | |
|---|---|---|
| 2011/0080554 A1 | 4/2011 | Toko |
| 2018/0193231 A1 | 7/2018 | Jung et al. |
| 2021/0007953 A1* | 1/2021 | Scheele ................. A61K 8/342 |

FOREIGN PATENT DOCUMENTS

| | | |
|---|---|---|
| JP | 5856628 B2 | 12/2015 |
| KR | 10-2011-0037905 A | 4/2011 |
| KR | 10-1498564 B1 | 3/2015 |
| KR | 10-1585635 B1 | 1/2016 |
| KR | 10-2017-0107169 A | 9/2017 |
| KR | 10-1884653 B1 | 8/2018 |
| KR | 10-1964666 B1 | 4/2019 |
| WO | 2012/123157 A1 | 9/2012 |
| WO | 2018/040412 A1 | 3/2018 |
| WO | 2021/259706 A1 | 12/2021 |

OTHER PUBLICATIONS

Helmenstine, Anne Marie, Ph.D. "Absolute Alcohol Definition and Formula." ThoughtCo, Jan. 10, 2018, https://web.archive.org/web/20180414045526/https://www.thoughtco.com/definition-of-absolute-alcohol-604996 (Year: 2018).*

Ina. How to make DIY soap dough. The Makeup Dummy. https://www.themakeupdummy.com/2017/06/15/4th-july-diy-soap-dough-bars/. (Year: 2017).*

Extended European Search Report dated Jun. 24, 2022, issued in EP22159165.4, 7 pages.

Communication pursuant to Article 94(3) EPC issued in European Application No. 22 159 165.4-1109 dated Jul. 28, 2023, 7 pgs.

* cited by examiner

*Primary Examiner* — Frederick F Krass
*Assistant Examiner* — Lucy M Tien
(74) *Attorney, Agent, or Firm* — Rothwell, Figg, Ernst and Manbeck, P.C.

(57) ABSTRACT

The present disclosure is directed to providing a moldable solid washing agent composition and an article molded from the same. The composition of the present disclosure can be stored easily at room temperature for a long time. It is applicable to a system that can be manufactured on site and can satisfy customer needs because it can be molded immediately by a simple method and the shape, size, etc. can be controlled. In addition, the solid washing agent composition disclosed in the present specification has superior compatibility with water.

14 Claims, 2 Drawing Sheets

[FIG. 1]
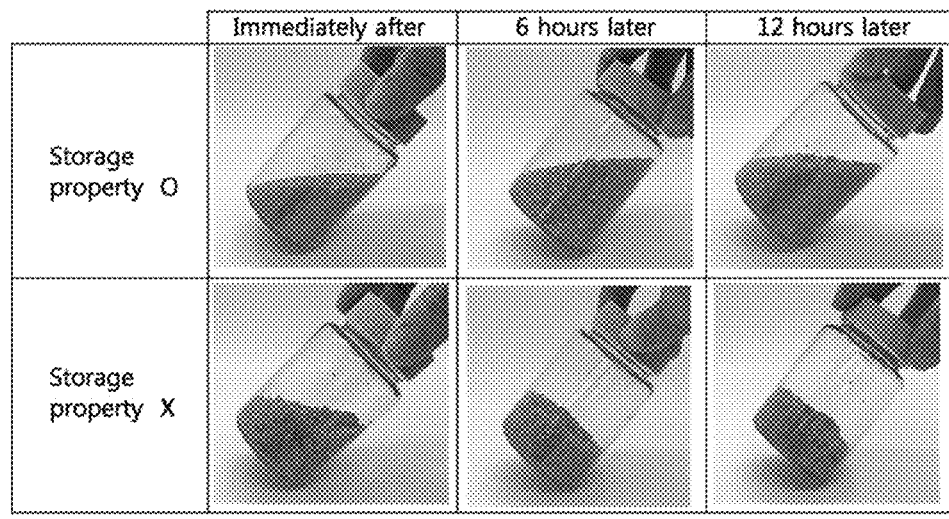
[FIG. 2]
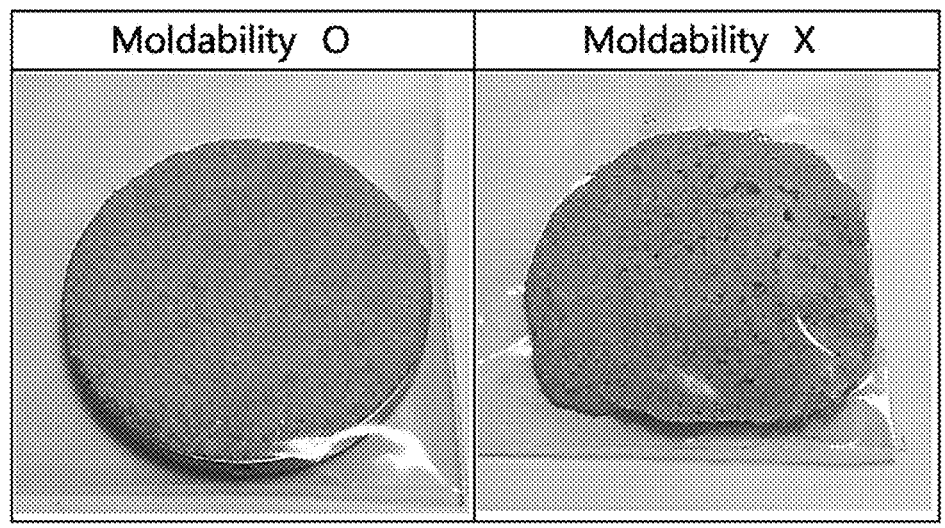

[FIG. 3]
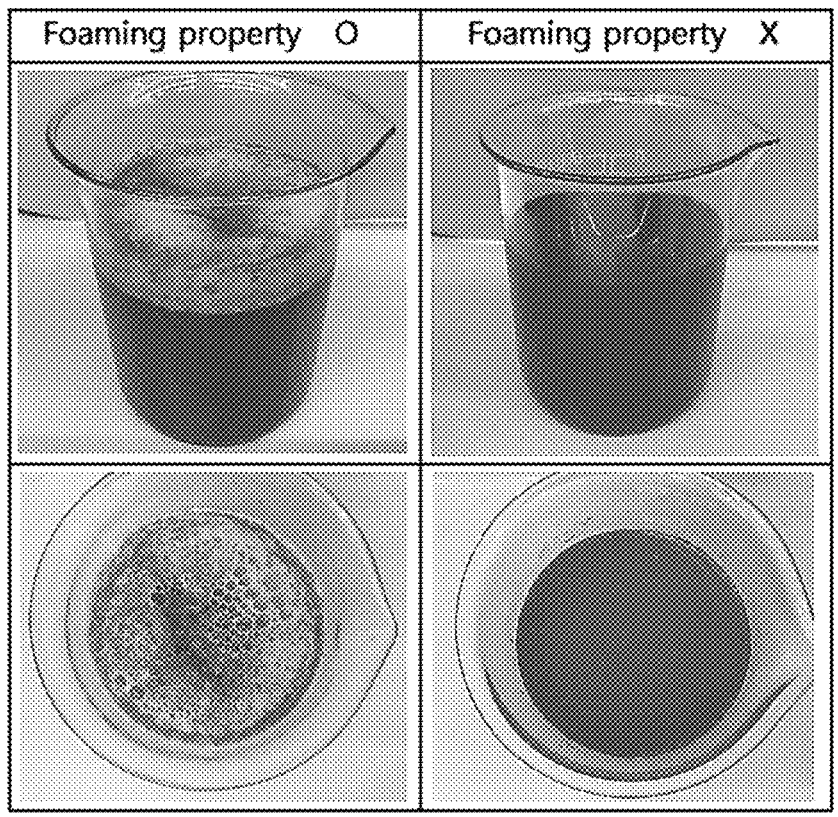
[FIG. 4]
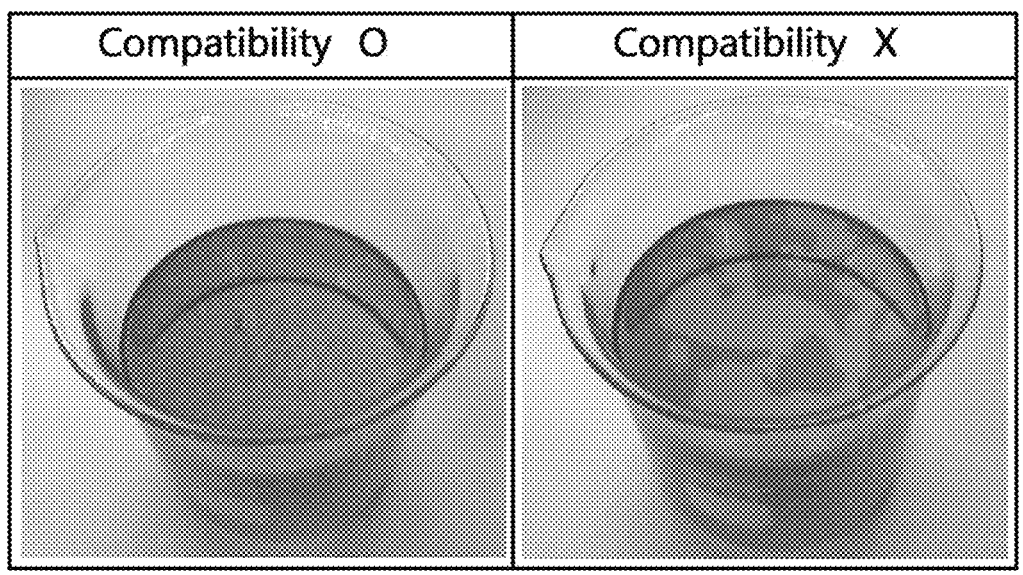

| # MOLDABLE COMPOSITION FOR SOLID WASHING AGENT AND METHOD FOR MOLDING THE SAME

TECHNICAL FIELD

The present specification discloses to a moldable composition for a solid washing agent and a method for molding the same.

CROSS-REFERENCE TO RELATED APPLICATION

This application claims the priority of Korean Patent Application No. 10-2021-0029532 filed on Mar. 5, 2021 and Korean Patent Application No. 10-2022-0014777 filed on Feb. 4, 2022, the contents of which in their entirety are incorporated herein by reference.

BACKGROUND ART

As customer needs are diversified, interests in on-site and customized cosmetics are increasing. However, because existing solid washing agents comprise solvents such as water for increasing reactivity upon mixing, it is difficult to satisfy storage property and moldability at the same time. Accordingly, they cannot be applied to systems that can be manufactured on site according to customer needs.

DISCLOSURE

Technical Problem

In an aspect, the present disclosure is directed to providing a solid washing agent composition which can be stored easily and exhibits superior moldability and an article molded from the same.

In another aspect, the present disclosure is directed to providing a solid washing agent composition which allows control of reactivity without water.

In another aspect, the present disclosure is directed to providing a method for molding a solid washing agent which can be molded immediately by a simple method according to customer needs.

Technical Solution

In an aspect, the present disclosure provides a moldable composition for a solid washing agent, which comprises a starch-based polymer and a polyol, wherein the starch-based polymer is comprised in an amount of more than 0 wt % and less than 20 wt % based on the total weight of the composition.

In an aspect, the present disclosure provides an article molded from the composition.

In an aspect, the present disclosure provides a method for molding a solid washing agent, which comprises a step of molding the composition described above by applying pressure.

Advantageous Effects

In an aspect, a solid washing agent composition disclosed in the present specification has superior storage property and moldability because it can maintain a formulation at room temperature for a long time without hardening. In another aspect, the solid washing agent composition disclosed in the present specification can be molded and solidified in short time by applying slight pressure at room temperature (25° C.) even without adding water.

In another aspect, when tepid water is added to the solid washing agent composition disclosed in the present specification, superior compatibility (or dispersibility) is achieved since oleophilic components are uniformly spread on the water surface without aggregation. In addition, because the oleophilic components are uniformly spread on the water interface, moisturizing components can be applied uniformly throughout the skin of the body.

BRIEF DESCRIPTION OF DRAWINGS

FIG. 1 shows a result of observing the storage property of a composition according to an exemplary embodiment of the present disclosure.

FIG. 2 shows a result of observing the moldability of a composition according to an exemplary embodiment of the present disclosure.

FIG. 3 shows a result of observing the foaming property of a composition according to an exemplary embodiment of the present disclosure.

FIG. 4 shows a result of observing the compatibility of a composition according to an exemplary embodiment of the present disclosure.

BEST MODE

Hereinafter, exemplary embodiments of the present disclosure are described in detail referring to the attached drawings. However, the technology disclosed in the present specification are not limited to the described exemplary embodiments but may be embodied in other forms. The exemplary embodiments are provided so that the present disclosure is thorough and complete and the technical idea of the present disclosure can be fully conveyed to those skilled in the art. Those having ordinary knowledge in the art will be able to embody the technical idea of the present disclosure in various other forms without departing from the technical idea of the present disclosure.

In the present specification, singular expressions comprise plural expressions unless the context clearly indicates otherwise. In the present disclosure, the terms such as "comprise", "contain", "include", "have", etc. are intended to indicate the existence of a feature, number, step, operation, part or combinations thereof described in the specification, and do not preclude the possibility of the presence or addition of one or more additional features, numbers, steps, operations, parts or combinations thereof.

Hereinafter, the present disclosure is described in detail.

In an exemplary embodiment, the present disclosure may provide a moldable solid washing agent composition, which comprises a starch-based polymer and a polyol, wherein the starch-based polymer is comprised in an amount of more than 0 wt % and less than 20 wt % based on the total weight of the composition.

In an exemplary embodiment, the present disclosure may provide a use of a starch-based polymer and a polyol for preparation of a moldable solid washing agent composition, wherein the composition comprises the starch-based polymer in an amount of more than 0 wt % and less than 20 wt % based on the total weight of the composition. In an exemplary embodiment, the present disclosure may provide a use of a starch-based polymer and a polyol for use in a moldable solid washing agent composition, wherein the composition comprises the starch-based polymer in an amount of more than 0 wt % and less than 20 wt % based on the total weight of the composition. In an exemplary embodiment, the present disclosure may provide a method for preparing a moldable solid washing agent composition which comprises adding a starch-based polymer and a polyol to a composition, wherein the composition comprises the starch-based polymer in an amount of more than 0 wt % and less than 20 wt % based on the total weight of the composition.

Since the composition according to an exemplary embodiment of the present disclosure does not comprise water and can be maintained in powder (granule) state at room temperature in a dispenser for 0-12 hours without hardening, it can be stored without additional reaction until customer order. In addition, the composition can be solidified by a simple method within about 3 minutes at room temperature and atmospheric atmosphere by applying pressure of 5-100 mbar without addition of water. Accordingly, in an exemplary embodiment, the composition may be prepared on site according to customer needs or may be prepared by a customer prior to use. In another exemplary embodiment, the composition may be stored in granule form and may be molded into a shape desired by a customer according to customer order. In another exemplary embodiment, the composition may be molded into a shape desired by a customer who has bought the composition prior to use.

In an exemplary embodiment, the composition may comprise water in an amount of less than 1 wt %, e.g., less than 1 wt %, less than 0.1 wt %, less than 0.01 wt %, less than 0.001 wt %, less than 0.0009 wt %, less than 0.0007 wt %, less than 0.0005 wt %, less than 0.0003 wt % or less than 0.0001 wt %, based on the total weight of the composition.

In an exemplary embodiment, the starch-based polymer may comprise one or more selected from a group consisting of corn starch, dextrin, hydroxypropyl starch phosphate and sodium polyacrylate starch. For example, the starch-based polymer may be obtained by mixing one or more selected from a group consisting of corn starch, dextrin, hydroxypropyl starch phosphate and sodium polyacrylate starch.

In an exemplary embodiment, the content of the starch-based polymer may be more than 0 wt % and less than 20 wt % based on the total weight of the composition. More specifically, the content of the starch-based polymer may be 0.1-15 wt % based on the total weight of the composition. For example, the content of the starch-based polymer may be more than 0 wt %, 0.01 wt % or more, 0.1 wt % or more, 0.5 wt % or more, 1 wt % or more, 2 wt % or more, 3 wt % or more, 4 wt % or more, 5 wt % or more, 6 wt % or more, 7 wt % or more, 8 wt % or more, 9 wt % or more, 10 wt % or more, 11 wt % or more, 12 wt % or more, 13 wt % or more, 14 wt % or more, 15 wt % or more, 16 wt % or more, 17 wt % or more, 18 wt % or more or 19 wt % or more, and less than 20 wt %, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.5 wt % or less, 0.4 wt % or less, 0.3 wt % or less, 0.2 wt % or less or 0.1 wt % or less. When the starch-based polymer is not comprised, molding may be difficult due to insufficient binding ability. And, when its content is 20 wt % or more, storage property and moldability may be negatively affected due to excessive stickiness.

In an exemplary embodiment, the polyol may comprise one or more selected from a group consisting of glycerin, butylene glycol, propylene glycol, dipropylene glycol, polyethylene glycol and sorbitol.

In an exemplary embodiment, the content of the polyol may be 0.1-10 wt % based on the total weight of the composition. For example, the content of the polyol may be 0.1 wt % or more, 0.5 wt % or more, 1 wt % or more, 2 wt % or more, 3 wt % or more, 4 wt % or more, 5 wt % or more, 6 wt % or more, 7 wt % or more, 8 wt % or more, or 9 wt % or more, and 10 wt % or less, 9 wt % or less, 8 wt % or less, 7 wt % or less, 6 wt % or less, 5 wt % or less, 4 wt % or less, 3 wt % or less, 2 wt % or less, 1 wt % or less or 0.5 wt % or less. When the content of the polyol is less than 0.1 wt %, molding may be difficult due to insufficient binding ability. And, when the content is more than 10 wt %, storage property or moldability may be insufficient due to excessive binding ability.

In an exemplary embodiment, the composition may further comprise a nonionic surfactant. Due to the solubilizing ability of an oil component, the nonionic surfactant can prevent aggregation of oil particles on the water surface by dispersing them, which is a characteristic necessary in terms of quality such as scent, moisturization, etc. Accordingly, when a foamable solid washing agent prepared from the composition according to an exemplary embodiment of the present disclosure is put in tepid water, superior compatibility may be achieved without aggregation of oleophilic components on the water surface.

In an exemplary embodiment, the nonionic surfactant may comprise one or more selected from a group consisting of an alkanolamide-based surfactant, an amine oxide-based surfactant, a mono- or polysaccharide-based surfactant, a fatty acid ethoxylate-based surfactant, a PEG-based surfactant, a polyethylene oxide-polypropylene oxide copolymer, a polyethylene oxide-polypropylene oxide-polyethylene oxide triblock copolymer, polyvinylpyrrolidone, a polyoxyethylene alkyl ether-based surfactant and a sorbitan-based surfactant.

For example, the nonionic surfactant may be cocamide methyl MEA, alkyl polyglucoside or polyoxyethylene sorbitan monolaurate.

In an exemplary embodiment, the content of the nonionic surfactant may be 0.1-5 wt %, for example, 0.1 wt % or more, 0.3 wt % or more, 0.5 wt % or more, 0.7 wt % or more, 0.9 wt % or more, 1 wt % or more, 2 wt % or more, 3 wt % or more or 4 wt % or more, and 5 wt % or less, 4 wt % or less, 3 wt % or less, 2 wt % or less, 1.8 wt % or less, 1.6 wt % or less, 1.4 wt % or less, 1.2 wt % or less, 1 wt % or less, 0.5 wt % or less or 0.3 wt % or less, based on the total weight of the composition.

The composition according to an exemplary embodiment may further comprise one or more selected from a group consisting of a pH control agent, an acid and an oil. When the solid washing agent composition comprising a pH control agent and an acid is added to water, foaming property may be achieved due to chemical reaction. In this aspect, the composition according to an exemplary embodiment may have foaming property. In addition, the composition according to an exemplary embodiment may further comprise an oil to provide moisturizing function. In the present specification, the term 'foaming' refers to the generation of carbon dioxide gas via chemical reaction when the composition according to an exemplary embodiment of the present disclosure is contacted with water. It is distinguished from bubbles or air bubbles formed as a surfactant having hydrophilic and oleophilic groups is disposed at the interface between water and air.

In an exemplary embodiment, the pH control agent may comprise sodium bicarbonate.

In an exemplary embodiment, the acid may comprise one or more selected from a group consisting of citric acid, lactic acid, maleic acid, acetic acid, phosphoric acid and tartaric acid.

In an exemplary embodiment, the oil may comprise one or more selected from a group consisting of argan oil, olive oil, castor oil, palm oil, avocado oil, almond oil, wheat germ oil, apricot kernel oil, evening primrose oil, rose hip oil, macadamia nut oil, liquid paraffin, isopropyl myristate, jojoba oil, green tea oil, sunflower seed oil and grape seed oil.

In an exemplary embodiment, the pH control agent may comprise sodium bicarbonate, the acid may comprise one or more selected from a group consisting of citric acid, lactic acid, maleic acid, acetic acid, phosphoric acid and tartaric acid, and the oil may comprise one or more selected from a group consisting of argan oil, olive oil, castor oil, palm oil, avocado oil, almond oil, wheat germ oil, apricot kernel oil, evening primrose oil, rose hip oil, macadamia nut oil, liquid paraffin, isopropyl myristate, jojoba oil, green tea oil, sunflower seed oil and grape seed oil.

In an exemplary embodiment, the content of the pH control agent may be 40-70 wt % based on the total weight of the composition. The content of the acid may be 15-45 wt % based on the total weight of the composition. The content of the oil may be 0.01-5 wt % based on the total weight of the composition.

For example, the content of the pH control agent may be 40 wt % or more, 45 wt % or more, 50 wt % or more, 55 wt % or more, 60 wt % or more or 65 wt % or more, and 70 wt % or less, 65 wt % or less, 60 wt % or less, 50 wt % or less, 45 wt % or less, 40 wt % or less or 35 wt % or less.

For example, the content of the acid may be 15 wt % or more, 20 wt % or more, 25 wt % or more, 30 wt % or more, 35 wt % or more or 40 wt % or more, and 45 wt % or less, 40 wt % or less, 35 wt % or less, 30 wt % or less, 25 wt % or less or 20 wt % or less.

For example, the content of the oil may be 0.01 wt % or more, 0.1 wt % or more, 1 wt % or more, 2 wt % or more, 3 wt % or more or 4 wt % or more, and 5 wt % or less, 4 wt % or less, 3 wt % or less, 2 wt % or less, 1 wt % or less or 0.1 wt % or less.

In an exemplary embodiment, the formulation of the composition may be a granule.

In an exemplary embodiment, 90% or more of the total particles of the composition may have a size of 1 μm to 5 mm. More specifically, 90% or more, 91% or more, 92% or more, 93% or more, 94% or more, 95% or more, 96% or more, 97% or more, 98% or more or 99% or more of the total particles of the composition may have a size of 1 μm to 5 mm. For example, the particles constituting the composition may have a size of 1 μm or larger, 10 μm or larger, 50 μm or larger, 100 μm or larger, 200 μm or larger, 300 μm or larger, 400 μm or larger, 500 μm or larger, 600 μm or larger, 700 μm or larger, 800 μm or larger, 900 μm or larger, 1 mm or larger, 1.5 mm or larger, 2 mm or larger, 2.5 mm or larger, 3 mm or larger, 3.5 mm or larger, 4 mm or larger, 4.5 mm or larger, 4.7 mm or larger or 4.9 mm or larger, and 5 mm or smaller, 4.5 mm or smaller, 4 mm or smaller, 3.5 mm or smaller, 3 mm or smaller, 2.5 mm or smaller, 2 mm or smaller, 1.5 mm or smaller, 1 mm or smaller, 900 μm or smaller, 800 μm or smaller, 700 μm or smaller, 600 μm or smaller, 500 μm or smaller, 400 μm or smaller, 300 μm or smaller, 200 μm or smaller, 100 μm or smaller, 50 μm or smaller, 10 μm or smaller or 5 μm or smaller.

In an exemplary embodiment, the composition may be a bath preparation. The bath preparation is not limited in size or shape as long as it is a solid formulation. For example, the bath preparation may be of a powder type or a lump type. More specifically, the bath preparation may be a bath bomb, a bath powder, a bubble bomb, a bubble bar, etc.

The composition according to an exemplary embodiment of the present disclosure may further comprise components comprised in general cosmetic compositions, if necessary. For example, it may further comprise an oil or fat, a humectant, an emollient, a surfactant, an organic or inorganic pigment, an organic powder, a sunscreen, an antiseptic, a sterilizer, an antioxidant, a plant extract, an alcohol, a colorant, a flavorant, a blood circulation promoter, a cooling agent, an antiperspirant, etc. In addition, it may further comprise a functional additive such as a water-soluble vitamin, an oil-soluble vitamin, a polypeptide, a polysaccharide, a sphingolipid and a seaweed extract, if necessary.

In an exemplary embodiment, the present disclosure may provide a molded article molded from the moldable solid washing agent composition described above. For example, the molded article may be a bath bomb. In an exemplary embodiment, a molded article with shape or size desired by a customer may be prepared using the composition described above. For example, a formulation such as a bath bomb may be molded immediately on site according to the customer's preference to satisfy the customer needs.

In an exemplary embodiment, the present disclosure may provide a method for molding a solid washing agent, which comprises a step of molding the composition by applying pressure.

Because a solid washing agent with a desired shape can be molded by a simple method of applying pressure as described above, a solid washing agent product satisfying the customer's preference can be provided on site.

In an exemplary embodiment, the pressure may be 5-100 mbar. For example, the pressure may be 5 mbar or higher, 7 mbar or higher, 10 mbar or higher, 13 mbar or higher, 16 mbar or higher, 19 mbar or higher, 22 mbar or higher, 25 mbar or higher, 28 mbar or higher, 30 mbar or higher, 35 mbar or higher, 40 mbar or higher, 45 mbar or higher, 50 mbar or higher, 55 mbar or higher, 60 mbar or higher, 65 mbar or higher, 70 mbar or higher, 75 mbar or higher, 80 mbar or higher, 85 mbar or higher, 90 mbar or higher or 95 mbar or higher, and 100 mbar or lower, 95 mbar or lower, 90 mbar or lower, 85 mbar or lower, 80 mbar or lower, 75 mbar or lower, 70 mbar or lower, 65 mbar or lower, 60 mbar or lower, 55 mbar or lower, 50 mbar or lower, 45 mbar or lower, 40 mbar or lower, 35 mbar or lower, 30 mbar or lower, 27 mbar or lower, 24 mbar or lower, 21 mbar or lower, 18 mbar or lower, 15 mbar or lower, 12 mbar or lower, 10 mbar or lower or 7 mbar or lower. If the pressure is outside the above ranges, molding may not be performed according to the shape of a mold.

In an exemplary embodiment, the pressure may be applied at room temperature and atmospheric atmosphere.

In an exemplary embodiment, the solid washing agent may be molded without using water.

Hereinafter, the present disclosure is described more specifically through examples. However, the following examples are provided only to help understanding the present disclosure and the scope of the present disclosure is not limited by them.

EXAMPLES

1. Effect of Content of Starch-Based Polymer

After preparing compositions according to the examples described in Table 1, storage property, moldability and foaming property were observed. Specifically, after mixing powder components in a mixer and then adding liquid components uniformly, the mixture was mixed again to prevent aggregation.

Storage property was evaluated as follows. After putting 30 g of a sample in a viscosity test bottle, it was investigated at room temperature whether the sample ran down well when the bottle was tilted by 45° immediately after preparation, 6 hours later or 12 hours later (n=6, each result was evaluated by 6 panels) (see FIG. 1).

Moldability was evaluated as follows. After putting 30 g of the sample in a circular mold and applying pressure of 5-100 mbar, it was observed with naked eyes whether the sample maintained its original shape well without being broken (n=6) (see FIG. 2).

Foaming property was evaluated as follows. After putting the molded sample in a transparent container holding tepid water, it was observed visually whether foaming occurred continuously as the sample was dissolved (n=6) (see FIG. 3).

TABLE 1

| Example (wt %) | 1-1 | 1-2 | 1-3 | 1-4 | 1-5 | 1-6 | 1-7 | 1-8 | 1-9 | 1-10 |
|---|---|---|---|---|---|---|---|---|---|---|
| Sodium bicarbonate | | | | To 100 | | | | | | To 100 |
| Citric acid | | | | 30 | | | | | | — |
| Glycerin | | | | 5 | | | | | | 5 |
| Cocamide methyl MEA | | | | 1 | | | | | | 1 |
| Fragrance | | | | 1 | | | | | | 1 |
| Hydroxypropyl starch phosphate | 0 | 5 | — | — | — | — | 0.1 | 15 | 20 | 5 |
| Sodium polyacrylate starch | — | — | 5 | — | — | — | — | — | — | — |
| VP/VA copolymer | — | — | — | 5 | — | — | — | — | — | — |
| Hydroxypropyl methylcellulose | — | — | — | — | 5 | — | — | — | — | — |
| Cellulose gum | — | — | — | — | — | 5 | — | — | — | — |
| Storage property | ○ | ○ | ○ | X | ○ | ○ | ○ | ○ | ○ | ○ |
| Moldability | X | ○ | ○ | X | X | X | ○ | ○ | X | X |
| Foaming property | ○ | ○ | ○ | ○ | ○ | ○ | ○ | ○ | ○ | X |

From FIG. 1, it can be seen that the example 1-4 showing poor (X) storage property was hardened without maintaining powder state. FIG. 1 also shows that the example 1-2 shows good (○) storage property.

FIG. 2 shows an example of testing moldability. The result of testing moldability is described in Table 1. From FIG. 2, it can be seen that the example 4-1 described in Table 4 has good (○) moldability, and the example 4-4 has poor (X) moldability. It can be seen that the composition having poor moldability breaks without maintaining its original shape.

From FIG. 3, it can be seen that the example 1-10 has poor (X) foaming property, and foaming due to carbon dioxide gas generation did not occur. FIG. 3 also shows that the example 1-2 has good (○) foaming property.

To conclude, it was confirmed that storage property and moldability can be satisfied simultaneously when the starch-based polymer is comprised as compared to other polymers (VP/VA copolymer, hydroxypropyl methylcellulose or cellulose gum). In addition, it was confirmed that good moldability can be achieved when the content of the starch-based polymer is less than 20 wt %.

2. Effect of Content of Polyol

After preparing compositions according to the examples described in Table 2, storage property, moldability and foaming property were observed.

TABLE 2

| Example (wt %) | 2-1 | 2-2 | 2-3 | 2-4 | 2-5 | 2-6 | 2-7 |
|---|---|---|---|---|---|---|---|
| Sodium bicarbonate | | | | To 100 | | | |
| Citric acid | | | | 30 | | | |
| Hydroxypropyl starch phosphate | | | | 10 | | | |
| Cocamide methyl MEA | | | | 1 | | | |
| Fragrance | | | | 1 | | | |
| Glycerin | — | 5 | — | — | 0.1 | 10 | 20 |
| 1,3-Butylene glycol | — | — | 5 | — | — | — | — |
| Dipropylene glycol | — | — | — | 5 | — | — | — |
| Storage property | ○ | ○ | ○ | ○ | ○ | ○ | X |
| Moldability | X | ○ | ○ | ○ | ○ | ○ | ○ |
| Foaming property | ○ | ○ | ○ | ○ | ○ | ○ | ○ |

As seen from Table 2, storage property, moldability and foaming property were superior when 1,3-butylene glycol, dipropylene glycol or glycerin was used. Superior storage property and moldability were achieved when the content of the polyol was 0.1-10 wt %.

3. Effect of Surfactant

After preparing compositions according to the examples described in Table 3, storage property, compatibility and foaming property were observed.

Compatibility was evaluated as follows. After putting the molded sample in a transparent container holding tepid water, it was observed visually whether the oil components were aggregated or uniformly dispersed on water surface (n=6) (see FIG. 4).

TABLE 3

| Example (wt %) | 3-1 | 3-2 | 3-3 | 3-4 | 3-5 |
|---|---|---|---|---|---|
| Sodium bicarbonate | | | To 100 | | |
| Citric acid | | | 30 | | |
| Hydroxypropyl starch phosphate | | | 10 | | |
| Glycerin | | | 5 | | |
| Fragrance | | | 1 | | |
| Cocamide methyl MEA | — | 1 | — | — | — |
| Cocamide MEA | — | — | 1 | — | — |
| Lauryl glucoside | — | — | — | 1 | — |
| Non-nonionic surfactant (disodium lauryl sulfosuccinate) | — | — | — | — | 1 |
| Storage property | ○ | ○ | ○ | ○ | ○ |
| Compatibility | X | ○ | ○ | ○ | X |
| Foaming property | ○ | ○ | ○ | ○ | ○ |

FIG. 4 shows that the composition of the example 3-2 has good (○) compatibility, whereas the composition of the example 3-1 has poor (X) compatibility with oil components separated and aggregated on the surface. As a result, it was confirmed that superior compatibility can be achieved when a nonionic surfactant is used.

4. Effect of Presence or Absence of Water

After preparing compositions according to the examples described in Table 4, storage property, moldability and foaming property were observed.

TABLE 4

| Example (wt %) | 4-1 | 4-2 | 4-3 | 4-4 |
|---|---|---|---|---|
| Sodium bicarbonate | To 100 | | | |
| Citric acid | 30 | | | |
| Hydroxypropyl starch phosphate | 10 | | | |
| Glycerin | 5 | | | |
| Fragrance | 1 | | | |
| Water | — | 0.5 | 1 | 3 |
| Storage property | ○ | ○ | X | X |
| Moldability | ○ | ○ | X | X |
| Foaming property | ○ | ○ | ○ | ○ |

As a result, it was confirmed that storage property and moldability can be satisfied at the same time when the composition comprises no water.

The present disclosure may provide the following exemplary embodiments.

A first exemplary embodiment may provide a moldable solid washing agent composition comprising a starch-based polymer and a polyol, wherein the starch-based polymer is comprised in an amount of more than 0 wt % and less than 20 wt % based on the total weight of the composition.

A second exemplary embodiment may provide the composition according to the first exemplary embodiment, wherein the composition comprises water in an amount of less than 1 wt % based on the total weight of the composition.

A third exemplary embodiment may provide the composition according to the first or second exemplary embodiment, wherein the starch-based polymer comprises one or more selected from a group consisting of corn starch, dextrin, hydroxypropyl starch phosphate and sodium polyacrylate starch.

A fourth exemplary embodiment may provide the composition according to any of the first to third exemplary embodiments, wherein the content of the starch-based polymer is 0.1-15 wt % based on the total weight of the composition. A fifth exemplary embodiment may provide the composition according to any of the first to fourth exemplary embodiments, wherein the polyol comprises one or more selected from a group consisting of glycerin, butylene glycol, propylene glycol, dipropylene glycol, polyethylene glycol and sorbitol.

A sixth exemplary embodiment may provide the composition according to any of the first to fifth exemplary embodiments, wherein the content of the polyol is 0.1-10 wt % based on the total weight of the composition.

A seventh exemplary embodiment may provide the composition according to any of the first to sixth exemplary embodiments, wherein the composition further comprises a nonionic surfactant.

An eighth exemplary embodiment may provide the composition according to any of the first to seventh exemplary embodiments, wherein the nonionic surfactant comprises one or more selected from a group consisting of an alkanolamide-based surfactant, an amine oxide-based surfactant, a mono- or polysaccharide-based surfactant, a fatty acid ethoxylate-based surfactant, a PEG-based surfactant, a polyethylene oxide-polypropylene oxide copolymer, a polyethylene oxide-polypropylene oxide-polyethylene oxide triblock copolymer, polyvinylpyrrolidone, a polyoxyethylene alkyl ether-based surfactant and a sorbitan-based surfactant.

A ninth exemplary embodiment may provide the composition according to any of the first to eighth exemplary embodiments, wherein the composition further comprises one or more selected from a group consisting of a pH control agent, an acid and an oil.

A tenth exemplary embodiment may provide the composition according to any of the first to ninth exemplary embodiments, wherein the pH control agent comprises sodium bicarbonate, and the acid comprises one or more selected from a group consisting of citric acid, lactic acid, maleic acid, acetic acid, phosphoric acid and tartaric acid, and the oil comprises one or more selected from a group consisting of argan oil, olive oil, castor oil, palm oil, avocado oil, almond oil, wheat germ oil, apricot kernel oil, evening primrose oil, rose hip oil, macadamia nut oil, liquid paraffin, isopropyl myristate, jojoba oil, green tea oil, sunflower seed oil and grape seed oil.

An eleventh exemplary embodiment may provide the composition according to any of the first to tenth exemplary embodiments, wherein the solid washing agent has foaming property.

A twelfth exemplary embodiment may provide the composition according to any of the first to eleventh exemplary embodiments, wherein the formulation of the composition is a granule.

A thirteenth exemplary embodiment may provide the composition according to any of the first to twelfth exemplary embodiments, wherein 90% or more of the total particles of the composition have a size of 1 μm to 5 mm.

A fourteenth exemplary embodiment may provide the composition according to any of the first to thirteenth exemplary embodiments, wherein the composition is a bath preparation.

A fifteenth exemplary embodiment may provide a molded article molded from the composition according to any of the first to fourteenth exemplary embodiments.

A sixteenth exemplary embodiment may provide the molded article according to the fifteenth exemplary embodiment, wherein the molded article is a bath bomb, a bath powder, a bubble bomb or a bubble bar.

A seventeenth exemplary embodiment may provide a method for molding a solid washing agent, which comprises a step of molding the composition according to any of the first to fourteenth exemplary embodiments by applying pressure.

An eighteenth exemplary embodiment may provide the method for molding a solid washing agent according to the seventeenth exemplary embodiment, wherein the pressure is 5-100 mbar.

A nineteenth exemplary embodiment may provide the method for molding a solid washing agent according to the seventeenth or eighteenth exemplary embodiment, wherein the pressure is applied at room temperature and atmospheric atmosphere.

A twentieth exemplary embodiment may provide the method for molding a solid washing agent according to the seventeenth to nineteenth exemplary embodiments, wherein the solid washing agent is molded without using water.

A twenty-first exemplary embodiment may provide a method for preparing a moldable solid washing agent composition according to any of the first to fourteenth exemplary embodiments, which comprises mix a starch-based polymer and a polyol, wherein the starch-based polymer is added in an amount of more than 0 wt % and less than 20 wt % based on the total weight of the composition.

A twenty-second exemplary embodiment may provide a method for preparing a moldable solid washing agent composition according to twenty-first exemplary embodiment, wherein the content of the polyol is 0.1-10 wt % based on the total weight of the composition.

A twenty-third exemplary embodiment may provide a method for preparing a moldable solid washing agent composition according to twenty-first exemplary embodiment or twenty-second exemplary embodiment, wherein the method further comprises adding one or more selected from a group consisting of a nonionic surfactant, a pH control agent, an acid and an oil.

The invention claimed is:

1. A moldable solid washing agent composition comprising a starch-based polymer, a polyol, and a surfactant, wherein the starch-based polymer is comprised in an amount of more than 0 wt % and less than 20 wt % based on the total weight of the composition,
   wherein the content of the polyol is 0.1-10 wt % based on the total weight of the composition,
   wherein the surfactant is a nonionic surfactant,
   wherein the content of the nonionic surfactant is 0.1-4 wt % based on the total weight of the composition,
   wherein the starch-based polymer is one or more selected from the group consisting of corn starch, dextrin, hydroxypropyl starch phosphate, and sodium polyacrylate starch,
   wherein the polyol is one or more selected from the group consisting of glycerin, butylene glycol, propylene glycol, dipropylene glycol, polyethylene glycol, and sorbitol,
   wherein the nonionic surfactant is one or more selected from the group consisting of an alkanolamide-based surfactant, an amine oxide-based surfactant, a mono- or polysaccharide-based surfactant, a fatty acid ethoxylate-based surfactant, a PEG-based surfactant, a polyethylene oxide-polypropylene oxide copolymer, a polyethylene oxide-polypropylene oxide-polyethylene oxide triblock copolymer, polyvinylpyrrolidone, a polyoxyethylene alkyl ether-based surfactant, and a sorbitan-based surfactant, and
   wherein an article can be molded from the composition by applying a pressure of 5-100 mbar to said moldable solid washing agent composition at room temperature and atmospheric pressure.

2. The composition according to claim 1, wherein the composition comprises water in an amount of less than 1 wt % based on the total weight of the composition.

3. The composition according to claim 1, wherein the content of the starch-based polymer is 0.1-15 wt % based on the total weight of the composition.

4. The composition according to claim 1, wherein the composition further comprises one or more selected from a group consisting of a pH control agent, an acid and an oil.

5. The composition according to claim 4, wherein
   the pH control agent comprises sodium bicarbonate,
   the acid comprises one or more selected from a group consisting of citric acid, lactic acid, maleic acid, acetic acid, phosphoric acid and tartaric acid, and
   the oil comprises one or more selected from a group consisting of argan oil, olive oil, castor oil, palm oil, avocado oil, almond oil, wheat germ oil, apricot kernel oil, evening primrose oil, rose hip oil, macadamia nut oil, liquid paraffin, isopropyl myristate, jojoba oil, green tea oil, sunflower seed oil and grape seed oil.

6. The composition according to claim 1, wherein the formulation of the composition is a granule.

7. The composition according to claim 1, wherein 90% or more of the total particles of the composition have a size of 1 μm to 5 mm.

8. A molded article molded from the composition according to claim 1, wherein the molded article is a bath bomb, a bath powder, a bubble bomb or a bubble bar.

9. A method for preparing a moldable solid washing agent composition according to claim 1, comprising mixing a starch-based polymer, a polyol, and a nonionic surfactant, wherein the starch-based polymer is added in an amount of more than 0 wt % and less than 20 wt % based on the total weight of the composition, wherein the content of the polyol is 0.1-10 wt % based on the total weight of the composition.

10. The method for preparing a moldable solid washing agent composition according to claim 9, wherein the method further comprises adding one or more selected from a group consisting of a pH control agent, an acid and an oil.

11. A method for molding a solid washing agent, comprising a step of molding the composition according to claim 1 by applying pressure.

12. The method for molding a solid washing agent according to claim 11, wherein the pressure is 5-100 mbar.

13. The method for molding a solid washing agent according to claim 11, wherein the pressure is applied at room temperature and atmospheric pressure.

14. The method for molding a solid washing agent according to claim 11, wherein the solid washing agent is molded without using water.

* * * * *